United States Patent
Petersen et al.

(10) Patent No.: US 10,900,024 B2
(45) Date of Patent: Jan. 26, 2021

(54) METHOD FOR PURIFYING VIRUSES OR VIRUS-LIKE PARTICLES USING A CROSSLINKED CELLULOSE HYDRATE MEMBRANE

(71) Applicant: Sartorius Stedim Biotech GmbH, Göttingen (DE)

(72) Inventors: Rebecca Petersen, Schifferstadt (DE); Kathrin Schröder-Tittmann, Göttingen (DE); Louis Villain, Hannover (DE)

(73) Assignee: Sartorius Stedim Biotech GmbH, Göttingen (DE)

( * ) Notice: Subject to any disclaimer, the term of this patent is extended or adjusted under 35 U.S.C. 154(b) by 0 days.

(21) Appl. No.: 16/329,512

(22) PCT Filed: Aug. 3, 2017

(86) PCT No.: PCT/EP2017/000943
§ 371 (c)(1),
(2) Date: Feb. 28, 2019

(87) PCT Pub. No.: WO2018/041389
PCT Pub. Date: Mar. 8, 2018

(65) Prior Publication Data
US 2019/0194627 A1    Jun. 27, 2019

(30) Foreign Application Priority Data

Sep. 1, 2016 (DE) ........................ 10 2016 010 601

(51) Int. Cl.
| | | |
|---|---|---|
| C12N 7/00 | (2006.01) | |
| B01J 20/24 | (2006.01) | |
| B01D 71/10 | (2006.01) | |
| B01J 20/28 | (2006.01) | |
| B01D 67/00 | (2006.01) | |
| B01J 20/00 | (2006.01) | |

(52) U.S. Cl.
CPC ........... *C12N 7/00* (2013.01); *B01D 67/0093* (2013.01); *B01D 71/10* (2013.01); *B01J 20/24* (2013.01); *B01J 20/28033* (2013.01); *B01D 2323/30* (2013.01); *B01J 20/00* (2013.01); *C12N 2710/00051* (2013.01); *C12N 2750/14051* (2013.01); *C12N 2795/00051* (2013.01)

(58) Field of Classification Search
None
See application file for complete search history.

(56) References Cited

U.S. PATENT DOCUMENTS 9,433,904 B2 *   9/2016   Demmer ............ B01J 20/28078
10,253,299 B2 *  4/2019   Villain ............... B01D 67/0093

FOREIGN PATENT DOCUMENTS

| EP | 3455349 | 3/2019 |
|---|---|---|
| WO | WO95/32793 | 12/1995 |
| WO | WO2009/127285 | 10/2009 |
| WO | WO2009/149067 | 12/2009 |
| WO | WO2012/169970 | 12/2012 |
| WO | WO2013/180650 | 12/2013 |
| WO | WO2014/133460 | 9/2014 |
| WO | WO2015/055269 | 4/2015 |
| WO | WO2017/076553 | 5/2017 |

OTHER PUBLICATIONS

International Search Report and Written Opinion for PCT/EP2017/000943, dated Nov. 7, 2017.
Sim, Siow-Leng et al., "Branched Polyethylene Glycol for Protein Precipitation," *Biotechnology and Bioengineering*, 109(3):739-746 (Mar. 2012).
Zalipsky, Samuel et al., "Introduction to Chemistry and Biological Application of Poly(ethylene glycol)," *ACS Symposium Series; American Chemical Society*, Chapter 1, 13 pages (Aug. 1997).

* cited by examiner

*Primary Examiner* — Agnieszka Boesen
(74) *Attorney, Agent, or Firm* — Klarquist Sparkman, LLP (57) ABSTRACT

The present invention relates to a method for purifying viruses or virus-like particles using a crosslinked cellulose hydrate membrane and to a kit for purifying viruses or virus-like particles and the use thereof.

13 Claims, 2 Drawing Sheets

METHOD FOR PURIFYING VIRUSES OR VIRUS-LIKE PARTICLES USING A CROSSLINKED CELLULOSE HYDRATE MEMBRANE

CROSS REFERENCE TO RELATED APPLICATIONS

This is the U.S. National Stage of International Application No. PCT/EP2017/000943, filed Aug. 3, 2017, which in turn claims the benefit of German Application No. 10 2016 010 601.8, filed Sep. 1, 2016, which application is incorporated herein in its entirety.

The present invention relates to a method for purifying viruses or virus-like particles from a solution, such as, for example, a bioprocess solution, using a crosslinked cellulose hydrate membrane and to a kit for purifying viruses or virus-like particles and the use thereof.

In recent years, the purification and isolation of viruses has gained in importance tremendously, especially in the pharmaceutical industry. After viruses have been cultured in cell cultures, it is necessary to separate the viruses from the contaminants, such as, for example, host cell proteins or deoxyribonucleic acid (DNA), so that they can be used further in pure form. In biopharmaceutical production processes, culturing leads to DNA and other proteins of the hosts occurring as by-products. These are generally part of the contaminants and must be removed from the end product during workup. Also in the production of viruses, DNA fragments of the hosts or viruses themselves are released, which must be removed.

In the prior art, viruses or virus-like particles are purified by using, for example, chromatographic methods. They are generally based on the chemical functionality of the surface of the solid phase and the associated interaction with the biomolecules in the mobile phase, which are bound by means of adsorption during flow-through of the chromatography medium. A disadvantage of these methods is that the binding of the viruses is achieved by means of the affinity for the ligands, this being a specific property of the viruses. Accordingly, different virus types require the use of different chromatography media having specific ligands in order to achieve high yields. Furthermore, certain environmental parameters, such as pH or conductivity, must be observed.

Also known in the prior art are separation methods which are primarily based on virus size (more precisely: hydrodynamic volume). These include density-gradient ultracentrifugation, which, for example, uses a cesium chloride (CsCl) solution for separating, inter alis, viruses on the basis of their density. Although this method delivers a high-purity separation of the different particles, said method has various disadvantages. In particular, the disadvantages of this method are high investment costs, long process times, CsCl contamination, high shear stress, and lack of scalability.

Another generally known method for purifying viruses from bioprocess solutions is size-exclusion chromatography (SEC) on chromatography gels. The disadvantages of this method are a low productivity and reduction in the virus concentration (dilution).

WO 2012/169970 A1 describes a method in which biological products, such as antibodies, viruses, cells, cell organelles or proteins, are purified by means of constrained cohydration chromatography or steric exclusion chromatography (SXC) on chromatography material, especially on starch powder or monolithic chromatography materials.

Owing to the large volumes which must be managed in virus purification (more particularly for vaccine production), monolithic chromatography materials are relatively expensive and less suited to single use.

It is therefore an object of the present invention to provide a cost-effective, rapid, robust and selective method for purifying viruses from a solution, which method is usable for a wide range of different types of viruses or virus-like particles, irrespective of their specific surface properties.

This object is achieved by the embodiments of the present invention that are characterized in the claims.

More particularly, the present invention provides a method for purifying viruses or virus-like particles from a solution, such as, for example, a bioprocess solution, comprising the following steps:
  a) providing a mixture M composed of a solution A, which contains the viruses or the virus-like particles to be purified and impurities, and a solution B, which contains polyalkylene glycol having two or three carbon atoms in the repeat unit,
  d) loading a crosslinked cellulose hydrate membrane with said mixture M from step a), with the viruses or the virus-like particles attaching to the outer and inner membrane surfaces and thus being retained, and
  f) eluting the viruses or virus-like particles retained in the crosslinked cellulose hydrate membrane using a solution which contains no polyalkylene glycol having two or three carbon atoms in the repeat unit or which contains at least 50% less polyalkylene glycol having two or three carbon atoms in the repeat unit than the mixture M from step a), with the result that the viruses or the virus-like particles are obtained in purified form in the eluate.

According to the present invention, the solutions are, above and below, aqueous solutions.

It was found that, surprisingly, addition of the polyalkylene glycol having two or three carbon atoms in the repeat unit to the solution composed of viruses or virus-like particles and application of this mixture to the crosslinked cellulose hydrate membrane result in the viruses or virus-like particles being retained during membrane flow-through and in the permeate solution being depleted of viruses or virus-like particles. As will be described in more detail below, it is possible, by selection of the molar mass and/or the concentration of the polyalkylene glycol having two or three carbon atoms in the repeat unit, to optimize the retention of the viruses or virus-like particles in the membrane such that only concentrations of the same of 1% and less can be detected in the permeate solution.

In a preferred embodiment, the loaded crosslinked cellulose hydrate membrane can be washed in a further step e) by application of a solution which contains as much polyalkylene glycol having two or three carbon atoms in the repeat unit as the solution with which the membrane was previously loaded, with the result that the impurities are flushed out of the membrane. However, the viruses or the virus-like particles continue to remain in the membrane. As a result of subsequent application to the membrane of a solution which contains no polyalkylene glycol having two or three carbon atoms in the repeat unit or which contains at least 50% less polyalkylene glycol having two or three carbon atoms in the repeat unit than the mixture M, the viruses or the virus-like particles are remobilized and eluted in purified form.

According to the present invention, the viruses are not subject to any particular restriction and include, for example, influenza viruses, yellow fever viruses, human papillomaviruses, vaccinia viruses, adenoviruses, adeno-associated viruses, baculoviruses, hepatitis viruses, lentiviruses, polio viruses, rabies viruses, rotaviruses, rubella viruses and zika viruses. According to the invention, virus-like particles (VLP) are understood to mean virus particles which contain no nucleic acids. Virus-like particles include viroids, virusoids and prions. Hereinafter, the viruses and the virus-like particles to be purified that are present in the solution, such as, for example, in the bioprocess solution, are subsumed under the term "viruses" for simplification.

Using the method according to the invention, it is possible to purify the different types of viruses irrespective of their chemical affinities. The method can be optimized using few method parameters, such as concentration and/or molar mass of the polyalkylene glycol having two or three carbon atoms in the repeat unit and/or contact time and/or residence time for the particular virus type, and can thus be used as platform technology.

Contact time defines the time interval in which the solution A, which contains the viruses or the virus-like particles to be purified and impurities, and the solution B, which contains polyalkylene glycol having two or three carbon atoms in the repeat unit, meet and form mixture M up to the time point at which the mixture M reaches the membrane.

Residence time defines the time interval in which the solution M resides in the membrane at the particular absolute flow rate. Thus, the residence time corresponds to the time interval which is available to the virus particles in the solution M for retention on the outer and inner surface of the membrane.

A further advantage of the method according to the invention is that viruses can be purified from an unpurified solution, but preferably clarified bioprocess solution, without having to set a certain pH or a certain conductivity. For example, the culture solution can be used directly after cell separation with the environmental buffer optimal for the viability of the virus. This buffer composition can be maintained over the entire method. This is a considerable advantage in comparison with known methods for virus purification, in which there is often the need for high salt concentrations and specific buffer systems, which may have an adverse effect on the viruses.

Moreover, the method according to the invention, compared to conventional chromatography methods, such as, for example, affinity chromatography, makes it possible to achieve very high relative flow rates, in membrane volumes (MV) per minute, of about 13 MV/min compared to 1 to 4 MV/min for affinity-chromatography columns.

Moreover, it was found that, surprisingly, the method according to the invention, using a crosslinked cellulose hydrate membrane having a particularly preferred pore size of from 3 to 5 μm, makes it possible to achieve a distinctly higher performance with respect to binding capacity compared to conventional hydrophilic chromatography materials and to affinity chromatography.

A further important aspect in the pharmaceutical industry is that this crosslinked cellulose hydrate membrane can, moreover, advantageously be sanitized before the method, for example by means of alkaline solutions, more particularly sodium hydroxide solution. Accordingly, the present method according to the invention preferably comprises a step b) of sanitizing with alkaline solution.

In a preferred embodiment of the method according to the invention, the solution A, which contains the viruses to be purified and impurities, and solution B, which contains polyalkylene glycol having two or three carbon atoms in the repeat unit, are mixed with the aid of a mixer, particularly preferably a static mixer. With the aid of the static mixer, it is possible within a short time to generate a homogeneous mixture composed of the solutions A and B with low shear stress on the viruses, because there are no movable mixer parts.

It is additionally advantageous that the contact time of the viruses or the virus-like particles with the solution B, which contains polyalkylene glycol having two or three carbon atoms in the repeat unit, is less than one minute before the loading step.

The method according to the invention can be adapted for the particular size and shape of the viruses to be purified by selection of the molar mass and/or the concentration of the polyalkylene glycol having two or three carbon atoms in the repeat unit. In general, the smaller the virus, the greater the necessary concentration of polyalkylene glycol having two or three carbon atoms in the repeat unit and/or the greater the necessary molar mass of the polyalkylene glycol having two or three carbon atoms in the repeat unit.

According to a preferred embodiment, the concentration of polyalkylene glycol having two or three carbon atoms in the repeat unit in the mixture M which is contacted with the crosslinked cellulose hydrate membrane is from 1 to 20, preferably from 5 to 18, particularly preferably from 8 to 15% by weight, based on the total mass of the mixture M.

According to a preferred embodiment, the polyalkylene glycol having two or three carbon atoms in the repeat unit is selected from the group consisting of polyethylene glycol (PEG) and polypropylene glycol or mixtures thereof.

The average molar mass of the polyalkylene glycol having two or three carbon atoms in the repeat unit is selected depending on the viruses to be purified. Preferably, the average molar mass of the polyalkylene glycol having two or three carbon atoms in the repeat unit is from 600 g/mol to 10 000 g/mol (daltons). Particularly preferably, the average molar mass of the polyalkylene glycol having two or three carbon atoms in the repeat unit is at least 1000 g/mol, more preferably at least 2000 g/mol, particularly preferably at least 3000 g/mol. The upper limit of the average molar mass of the polyalkylene glycol having two or three carbon atoms in the repeat unit is preferably 9000 g/mol, more preferably 8000 g/mol.

According to a further preferred embodiment, the recovery rate for purified viruses in the eluate is more than 50%, more preferably 55% or more, and particularly preferably 60% or more.

Furthermore, it is preferred that the concentration of the viruses in the eluate is elevated by a factor of ≥5, particularly preferably ≥10, in comparison with the starting solution, preference also being given to a range from a factor of 5 to a factor of 10 according to the present invention.

The present invention further provides a kit for purifying viruses or virus-like particles from a solution A, such as, for example, a bioprocess solution which is preferably clarified, but can be unpurified, at least comprising a solution B, which contains polyalkylene glycol having two or three carbon atoms in the repeat unit, and a crosslinked cellulose hydrate membrane. In this connection, the solution A is mixed with the solution B and guided as mixture M through the crosslinked cellulose hydrate membrane. The above and following remarks concerning the method according to the invention therefore also apply to the kit according to the invention. The crosslinked cellulose hydrate membrane is preferably arranged in a multilayer manner within a filter unit having at least one inlet for the mixture M and one outlet for permeate, with a mixer, preferably a static mixer, connected to reservoirs for the solutions A and B being upstream of the inlet. For single use, at least the abovementioned components of the device are preferably made of plastic.

Reusable parts of further components, such as pumps, valves, sensors, can be made of other materials.

The kit according to the invention is preferably used for purifying viruses or virus-like particles in vaccine production as a disposable product (single-use product) for single use.

As described above, the present invention provides a method for purifying viruses or virus-like particles also from a solution, such as, for example, a bioprocess solution, especially after cell separation (clarification), in which method a) a solution A, which contains viruses or virus-like particles and impurities, is admixed with a solution B, which contains polyalkylene glycol having two or three carbon atoms in the repeat unit, and both solutions are mixed, d) this thus prepared mixture M is guided across a crosslinked cellulose hydrate membrane, e) optionally the membrane is washed with a solution which contains as much polyalkylene glycol having two or three carbon atoms in the repeat unit as the mixture M, and f) subsequently an elution solution which contains no polyalkylene glycol having two or three carbon atoms in the repeat unit or which contains at least 50% less polyalkylene glycol having two or three carbon atoms in the repeat unit than the mixture M is applied to the membrane, resulting in the viruses or virus-like particles being eluted in purified form.

In the method according to the invention, viruses are separated off from the solution, such as, for example, the bioprocess solution. According to the invention, the (aqueous) virus solution is not subject to any particular restriction and can contain impurities (contaminants), such as, for example, nucleic acids, cellular proteins, endotoxins or other contaminants, in addition to the viruses to be purified. For the purification, the chemical interactions between the membrane surface and the viruses to be purified are negligible.

The (aqueous) solutions A and B used in the method according to the invention can further contain a buffer tailored to the viruses. As explained above, the salt concentration of said solutions A and B can moreover be freely adjusted depending on the solution to be purified. According to the invention, the clarified bioprocess solution is preferably used as solution A and can accordingly contain further components, such as, for example, a buffer and/or salts, in addition to the viruses and impurities (contaminants). The same applies to the solution B, which contains polyalkylene glycol having two or three carbon atoms in the repeat unit.

Accordingly, it would be possible for the solutions A and B to be also referred to as buffer solutions A and B.

Preferably, the method according to the invention comprises the following steps:

c) Equilibration

In an optional equilibration step, the crosslinked cellulose hydrate membrane is flushed with a buffer-containing solution B, which contains polyalkylene glycol having two or three carbon atoms in the repeat unit, until a constant conductivity and/or a constant UV signal have appeared in the permeate. The buffer composition and the conductivity are selected such that there are optimum conditions for the particular virus type. The selected concentration and molar mass of the polyalkylene glycol having two or three carbon atoms in the repeat unit is dependent on the virus type.

d) Loading

The buffer solution A (e.g., clarified cell-culture solution) and the buffer solution B are mixed in an appropriate ratio (step a)), setting the desired concentration of polyalkylene glycol having two or three carbon atoms in the repeat unit. Thereafter, this mixture M composed of the buffer solutions A and B is guided through a membrane module, which contains the crosslinked cellulose hydrate membrane, and said mixture is loaded.

e) Washing

In an optional step, the membrane can be flushed with a solution which contains as much polyalkylene glycol having two or three carbon atoms in the repeat unit as the mixture M composed of the buffer solutions A and B.

f) Elution

A buffer solution which contains no polyalkylene glycol having two or three carbon atoms in the repeat unit or which contains at least 50% less polyalkylene glycol having two or three carbon atoms in the repeat unit than the mixture M composed of the buffer solutions A and B is applied to the membrane. As a result, the viruses retained in the membrane elute from the membrane as eluate in the purified and preferably concentrated state.

It is known that the viscosity of the solution increases as the concentration of polyalkylene glycol having two or three carbon atoms in the repeat unit rises. For example, a 10% solution of polyalkylene glycol having two or three carbon atoms in the repeat unit with a molar mass of 6000 g/mol, such as, for example, the polyethylene glycol (PEG) PEG 6000, in water has, at 25° C., already a viscosity higher than water by more than four times, whereas the viscosity of a 20% solution of polyethylene glycol PEG 6000 in water is more than eleven times higher than water. However, a higher viscosity is associated with a decrease in the flow rate and has accordingly an adverse effect on the productivity of the separation process. On the other hand, the presence of polyalkylene glycol having two or three carbon atoms in the repeat unit in the solution B makes it possible for viruses to be retained by the membrane despite the relatively large pore size.

It has become apparent that very small viruses, such as, for example, adeno-associated virus (AAV2), or small phages, such as, for example, phi X 174, which have an average particle diameter of approx. 22 nm and 25 nm respectively, require a concentration of polyalkylene glycol having two or three carbon atoms in the repeat unit, such as, for example, PEG, of 10% or more, preferably of 11% or more, particularly preferably of 12% or more, at an average molar mass of 6000 g/mol, in order to achieve high yields and purities. However, in the case of these concentrations, conditions exist, under which the viruses of this size are normally precipitated in the presence of polyalkylene glycol having two or three carbon atoms in the repeat unit, such as, for example, PEG. However, it has been found that, surprisingly, the use of a mixer and preferably of a static mixer and the realization of very short contact times before membrane application avoid a precipitation of the viruses and can achieve high recovery rates and purities.

According to the present invention, the contact time of the viruses with the solution B, which contains polyalkylene glycol having two or three carbon atoms in the repeat unit, before the loading step is preferably less than one minute. This is preferably achieved by intensely mixing the solutions A and B with the aid of a mixer and particularly preferably a static mixer and guiding them directly after the mixer through the membrane module containing the crosslinked cellulose hydrate membrane. As a result, it is advantageously possible that a precipitation of the viruses can be avoided.

A further important aspect of the present invention is that the viruses can be purified on the basis of the method according to the invention by, for example, it being possible to use a culture solution directly after cell separation without the prior need to set a certain pH or a certain conductivity. Accordingly, a buffer composition optimal for the viability of the virus can be used over the entire method.

WO 2012/169970 A1 discloses that a high salt concentration in the SXC on starch powder or monolithic chromatography materials leads to a dramatic decline in the binding capacity. According to the present invention, it has become apparent that no significant losses in the recovery rates occur even at high salt concentrations, for example in the case of a 500 mM NaCl solution.

According to the present invention, the viruses are purified with the aid of a crosslinked cellulose hydrate membrane. According to the invention, use is made of porous, planar cellulose hydrate membranes, which thus distinctly differ from chromatographic columns, etc. They are not subject to any particular restriction, provided that they are crosslinked cellulose hydrate membranes having preferably a pore size of from 0.5 to 10 µm, particularly preferably from 3 to 5 µm. Such membranes are known in the prior art and also commercially available, for example as Hydrosart® membrane from the patent applicant.

According to WO 1995/032793 A1, the crosslinked cellulose hydrate membrane is produced using at least one crosslinker having at least 2 functional groups in the molecule that are reactive with the hydroxyl groups of the cellulose. Such crosslinkers can be diepoxides, such as 5,6-diepoxyhexane, glycidyl ethers, such as 1,4-butanediol diglycidyl ether, ethylene glycol diglycidyl ether, glycerol diglycidyl ether, polyethylene glycol diglycidyl ether, epichlorohydrin, epibromohydrin, alkylene dihalogen or hydroxyalkylene dihalogen compounds.

Moreover, the use of a crosslinked cellulose hydrate membrane having a pore size of preferably from 0.5 to 10 µm, particularly preferably from 3 to 5 µm, allows high membrane loading, this leading to a high binding capacity compared to conventional hydrophilic chromatography materials. As demonstrated in the examples below, the binding capacity, based on the volume of the solid phase, as per one embodiment according to the invention is greater by at least a factor of 10 than in the case of conventional chromatography materials, such as affinity-chromatography columns.

The use of a crosslinked cellulose hydrate membrane having a pore size greater than 1 µm allows distinctly higher permeabilities for the viscous solutions which contain polyalkylene glycol having two or three carbon atoms in the repeat unit.

In comparison with uncrosslinked cellulose hydrate membranes, the crosslinked cellulose hydrate membranes are distinguished by distinctly higher permeabilities after sanitization.

According to the invention, the crosslinked cellulose hydrate membrane can be used either as a reinforced membrane or as an unreinforced membrane, preference being given to using reinforced cellulose hydrate membranes. Suitable reinforcements are, for example, nonwoven fabric or woven fabric.

As described above, very high absolute flow rates can be achieved using the method according to the invention in comparison with conventional chromatography methods, making it possible to achieve a reduction in the contact times before membrane application. As a result, it is possible to avoid a precipitation of the viruses and to achieve high recovery rates and purities.

According to a preferred embodiment of the present invention, the recovery rate for purified viruses in the eluate is more than 50%. In comparison with a conventional affinity-chromatography method, the method according to the invention achieves a virus concentration in the eluate that is higher by, for example, a factor of 10 than in the starting solution.

The present invention will be more particularly elucidated on the basis of the following nonlimiting examples and figures.

EXAMPLES

Exemplary Embodiment 1: Purification of Bacteriophage phi X 174 from the Clarified Process Solution The phages to be purified were first generated by infection of a bacteria culture (*E. coli* C600) in TSB buffer. After the bacteria had been separated off by means of filtration through two filter systems (SartopurePP2 & Sartopore 2, both from Sartorius Stedim Biotech GmbH), there was a phage concentration of $3.8 \times 10^{11}$ particles/mL. This solution will be referred to below as "phage solution".

For the chromatographic purification, use was made of a Hydrosart® membrane (Sartorius Stedim Biotech GmbH), i.e., a crosslinked cellulose hydrate membrane, having a pore size of from 3 to 5 µm. A filtration unit, Vivapure® system (SSB, Göttingen), containing the cellulose hydrate membrane and having a membrane volume (MV) of 0.023 mL was connected to an Äkta system (Äkta Prime, GE Healthcare Life Science). Over the experiment, the absolute flow rate was constantly 0.3 mL/min, which corresponds to a relative flow rate of approx. 10 MV/min. The membrane was first equilibrated with a mixture composed of buffer A (50 mM Tris (Merck Millipore), pH 7.0, 150 mM NaCl (Merck Millipore)) and buffer B (50 mM Tris, pH 7.0, 150 mM NaCl, 16% by weight of PEG 6000 (Mw=6000 g/mol, Carl Roth)) in the ratio of 1:4. The final concentration of PEG 6000 in the mixture was 12% by weight.

For the loading, buffer A was replaced with the phage solution. The mixing operation was done in-line in a static mixer of the Äkta system. After altogether 55 mL of solution (13.7 mL of phage solution and 41.3 mL of buffer B) had been loaded, the membrane was washed. To this end, a mixture composed of buffer A and buffer B in the ratio of 1:4 was used again. The phage particles were eluted from the membrane by using 100% buffer A. The phage recovery was 81.6% (±3%).

The virus particles were quantified by means of quantitative real-time PCR on an instrument from Agilent Technologies (Mx3005P qPCR system) using the master mix Brilliant III Ultra-Fast SYBR® Green QPCR from Agilent Technologies. The reference used was a plasmid bearing the sequence of the phi X 174 phage (Fermentas GmbH).

The depletion of contaminants with simultaneous enrichment of phage particles was quantified by carrying out size-exclusion chromatography (SEC). To this end, a SEC column (Yarra 3000, Phenomenex) was connected to an HPLC system (UltiMate 3000, Thermo Scientific Dionex) and a 100 µl sample was loaded in each case. The absolute flow rate was 1 ml/min and the composition of the running buffer was as follows: 100 mM sodium phosphate and 100 mM sodium sulfate (pH=6.6).

Figure 1:
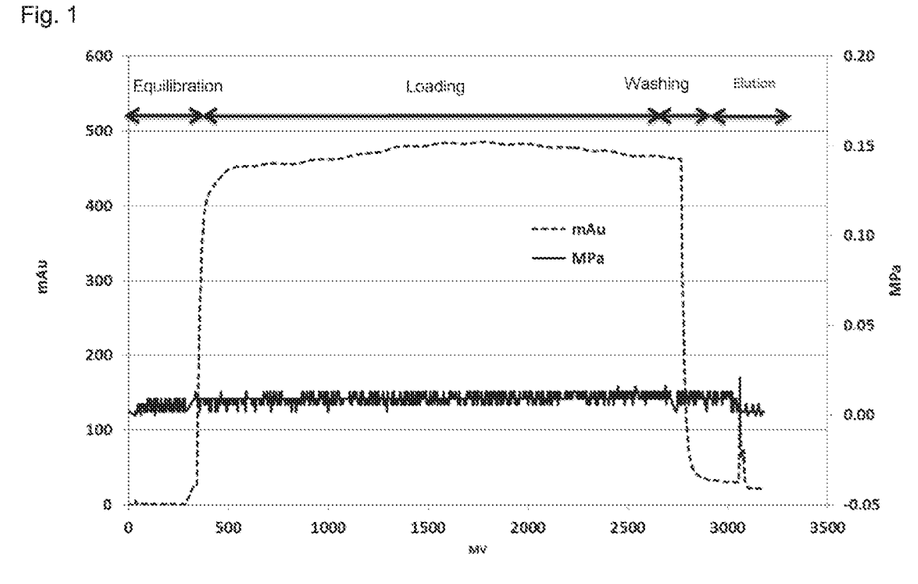
FIG. 1 shows, by way of example, the course of the purification of phi X 174 from Exemplary Embodiment 1 comprising the steps of equilibration, loading, washing and elution.

FIG. 1 shows, by way of example, the course of the purification of phi X 174 from Exemplary Embodiment 1 comprising the steps of equilibration, loading, washing and elution.

Figure 2:
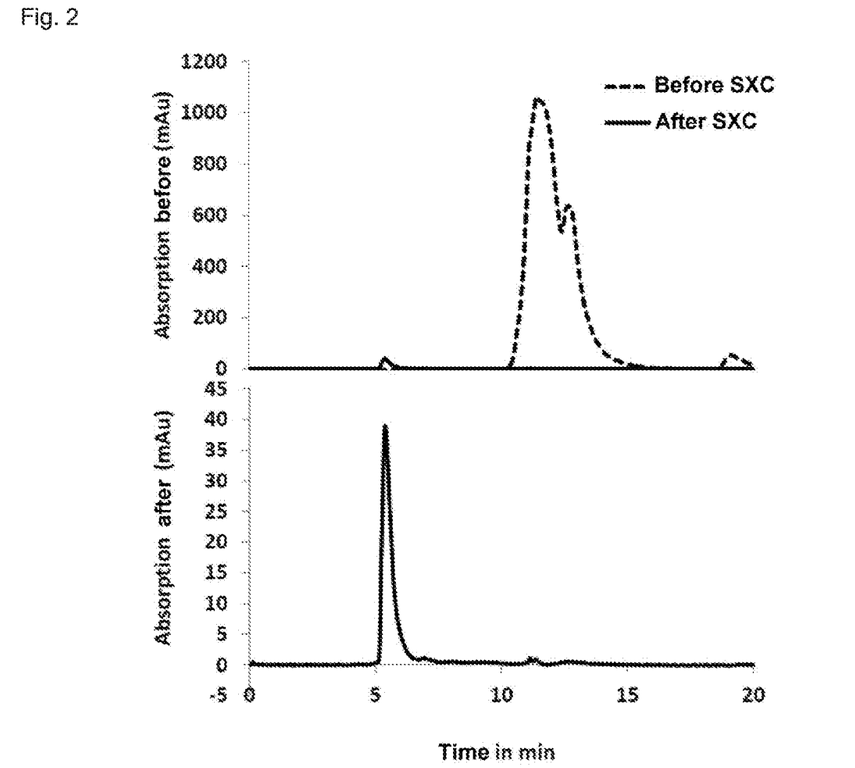
FIG. 2 shows the purification efficiency of the method according to the invention for phi X 174 as an example, measured using size-exclusion chromatography, by means of the chromatogram before and after the purification.

FIG. 2 shows the purification efficiency of the method for phi X 174 as an example, measured using size-exclusion chromatography, by means of the chromatogram before and after the purification. The impurities (large peak at 12 min) disappear completely and the chromatogram shows only the pure phage peak at approx. 6 min.

Exemplary Embodiment 2: Purification of Bacteriophage phi X 174 from the Clarified Process Solution with Relatively Short Contact Time The method was carried out in line with Exemplary Embodiment 1 on two further crosslinked cellulose hydrate membrane-containing filtration units which had a higher membrane volume of a) 0.046 mL and b) 0.56 mL compared to Exemplary Embodiment 1. As in Exemplary Embodiment 1, the relative flow rate was adjusted to approx. 10 MV/min in both cases. Owing to the altered membrane volumes compared to Exemplary Embodiment 1, the respective absolute flow rates changed from 0.3 mL/min in Exemplary Embodiment 1 to a) 0.6 mL/min and b) 5.6 mL/min. At the same time, the desired reduction in the contact time from 16.9 min in Exemplary Embodiment 1 to a) 8.3 min and b) 0.93 min appeared with the increase in the absolute flow rate. The experiments were carried out twice in both cases, and the results are depicted in Table 1.

A reduction in the contact time from 16.9 min in Exemplary Embodiment 1 to 2a) 8.3 min showed no significant effect on the recovery rate and binding capacity. However, the reduction in the contact time to less than 1 min in 2b) led to a distinct improvement in the recovery rate to more than 97% with, simultaneously, approx. 0% recovery rate in the permeate.

TABLE 1

Overview of parameters and results in the purification of bacteriophage phi X 174 on crosslinked cellulose hydrate membranes for various membrane volumes (MV)

|  | Example 1 | Example 2a) | Example 2b) |
| --- | --- | --- | --- |
| MV in mL | 0.023 | 0.046 | 0.56 |
| Absolute flow rate in mL/min | 0.3 | 0.6 | 5.6 |
| Contact time in min | 16.9 | 8.4 | 0.93 |
| Recovery in the eluate in % | 81.6 ± 3 | 79.0 ± 0 | 97.4 ± 0.7 |
| Recovery in the permeate in % | 0.7 ± 0.3 | 1.0 ± 0 | 0.05 ± 0.01 |
| Binding capacity (particles/mL MV) | $1.6 \times 10^{14}$ | $1.7 \times 10^{14}$ | $2.5 \times 10^{14}$ |

Figure 3:
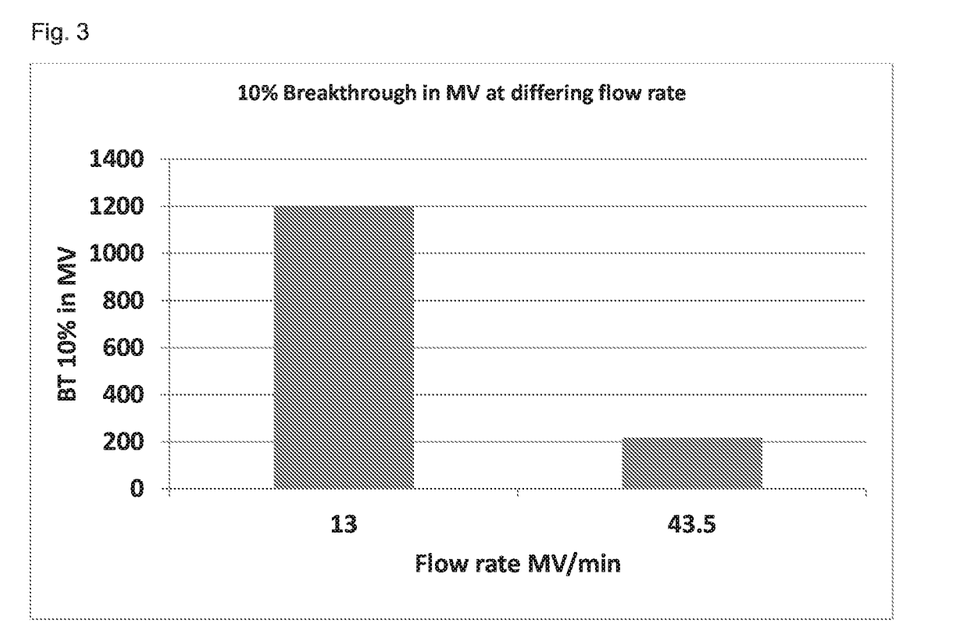
FIG. 3 shows the dynamic binding capacity in the purification of bacteriophage phi X 174 from Exemplary Embodiment 3.

Exemplary Embodiment 3: Purification of Bacteriophage phi X 174 from the Clarified Process Solution for Various Residence Times in the Membrane The method was carried out in line with Exemplary Embodiment 1 on a filtration unit, Vivapure® system (SSB, Göttingen), containing the crosslinked cellulose hydrate membrane and having a membrane volume of 0.023 mL, but having an absolute flow rate of 1 ml/min, with the relative flow rate increasing compared to Exemplary Embodiment 1 from 13 MV/min to 43.5 MV/min, and as a result the residence time simultaneously decreasing from 4.6 sec to 1.4 sec. The dynamic binding capacity (DBC 10%), at which a 10% breakthrough of the phage particles, based on the starting solution, could be detected, was calculated. The results are depicted in Table 2 and in FIG. 3. In the case of a residence time of 4.6 sec, the 10% breakthrough of the phage particles, based on the starting solution, was achieved at about 1200 membrane volume (MV), and in the case of a residence time of only 1.4 sec, this was achieved as early as at approx. 200 membrane volume (MV). As a result of an increase in the residence time, it was thus possible to increase, by a factor of 6, the maximum volume of the phage solution that can be purified across the filtration unit before the 10% breakthrough of the phage particles, based on the starting solution.

TABLE 2

Overview of parameters and results in the purification of bacteriophage phi X 174 on crosslinked cellulose hydrate membranes for various residence times

|  | Example 1 | Example 3 |
| --- | --- | --- |
| MV in mL | 0.023 | 0.023 |
| Absolute flow rate in mL/min | 0.3 | 1.0 |
| Relative flow rate in MV/min | 13 | 43.5 |
| Residence time in sec | 4.6 | 1.4 |
| DBC 10% in MV | 1200 | 200 |

Exemplary Embodiment 4: Purification of Bacteriophage phi X 174 from the Clarified Process Solution for Various Conductivities The method was carried out in line with Exemplary Embodiment 1 on a filtration unit, Vivapure® system (SSB, Göttingen), containing the crosslinked cellulose hydrate membrane and having a membrane volume of 0.023 mL, but having a salt concentration in buffer A and B of 500 mM sodium chloride. The PEG concentration used in the context of the experimental plan was 11% in this series of experiments; therefore, the recovery rates are altogether lower than in the case of 12% PEG. The experiment was carried out twice. There is no significant influence of the salt concentration on the recovery rate, as can be seen on the basis of the results shown in Table 3.

TABLE 3

Recovery rate in the purification of bacteriophage phi X 174 from the clarified process solution for various conductivities

|  | Example 1 | Example 4 |
| --- | --- | --- |
| MV in mL | 0.023 | 0.023 |
| Absolute flow rate in mL/min | 0.3 | 0.3 |

TABLE 3-continued

Recovery rate in the purification of bacteriophage phi X 174 from the clarified process solution for various conductivities

| | Example 1 | Example 4 |
|---|---|---|
| NaCl concentration in mmol | 150 | 500 |
| Recovery in the eluate in % | 64.6 ± 1.0 | 72.6 ± 2.8 |

Exemplary Embodiment 5: Purification of Adeno-Associated Virus (AAV2) from Biotechnological Solution The adeno-associated virus particles (AAV2) were produced using HEK 293 T (ATCC® CRL-3216™). The cells were transfected using plasmids. The AAV2 stock solution was treated with Benzonase (30 units/ml), clarified by centrifugation (300×g, where g=gravity, for 20 min at 4° C.) and filtered across 0.2 µm sterile filters (Minisart®, Sartorius Stedim Biotech GmbH). This solution is called "AAV2 solution".

The purification was carried out on a filtration unit, Vivapure® (SSB, Göttingen), containing the crosslinked cellulose hydrate membrane and having a pore size of from 3 to 5 µm and a membrane volume of 0.046 mL, connected to an Äkta system (Äkta Prime, GE Healthcare Life Science). Over the experiment, the absolute flow rate was constantly 0.6 mL/min. The membrane was first equilibrated with a mixture composed of buffer A (0.5 M NaCl, 0.05 M Tris, pH 7.0, conductivity 53.7 mS/cm) and buffer B (16% by weight of PEG 6000, 0.5 M NaCl, 0.05 M Tris, pH=7.0, conductivity 24.4 mS/cm) in the ratio of 1:4. The final concentration of PEG 6000 in the mixture was 12% by weight.

For the binding of the AAV2 particles, buffer A was replaced with the AAV2 solution. The mixing operation was done in-line in a static mixer of the Äkta system. After altogether 55 mL of solution (13.7 mL of AAV2 solution and 41.3 mL of buffer B) had been loaded, the membrane was washed. To this end, a mixture composed of buffer A and buffer B in the ratio of 1:4 was used again. The AAV2 particles were eluted from the membrane by using 100% buffer A.

The AAV2 particles were quantified by means of quantitative real-time PCR on an instrument from LightCycler® 480 (Roche Life Science) using the master mix LightCycler Faststart Master SYBR Green. The reference used was an internally produced plasmid bearing the sequence of the AAV2 particle.

The recovery rate of the purified AAV2 particle was 81.8%, with simultaneous breakthrough of 0.18% in the permeate and 0.15% in the wash solution. The binding capacity was $2.52 \times 10^{13}$ particles per mL of membrane volume.

For comparison, the purification of the AAV2 particles from the same biotechnological solution was carried out using the method of affinity chromatography. To this end, the virus solution was guided across a chromatography column, packed with AVB Sepharose affinity resin, having a column volume of 0.2 ml at a flow rate of 1.2 ml/min.

The recovery rate of the affinity chromatography-purified AAV2 particles was 30.0%. The binding capacity was $1.82 \times 10^{12}$ particles per mL of membrane volume.

The results in Table 4 show that the purification method described according to the invention achieves a binding capacity higher by a factor of 10 compared to conventional affinity chromatography. Similarly, a higher recovery rate (recovery) is achieved.

TABLE 4

Overview of parameters and results in the purification of AAV2 on crosslinked cellulose hydrate membranes on Hydrosart® compared to the conventional affinity-chromatography method

| | Purification as per method according to the invention | Affinity chromatography |
|---|---|---|
| MV in mL | 0.046 | 0.2 |
| Particle concentration in the starting solution in particles/mL | $1.42 \times 10^{12}$ | $1.42 \times 10^{12}$ |
| Particle concentration in the breakthrough in particles/mL | $2.62 \times 10^{9}$ | $2.08 \times 10^{11}$ |
| Particle concentration in the eluate in particles/mL | $1.16 \times 10^{12}$ | $3.64 \times 10^{11}$ |
| Binding capacity in particles/mL MV | $2.52 \times 10^{13}$ | $1.82 \times 10^{12}$ |
| Recovery rate in the eluate in % | 81.8 | 30.0 |

Exemplary Embodiment 6: Purification of Adenovirus Type 5 from Biotechnological Solution The adenovirus type 5 particles (AD5) were produced using HEK 293 (ATCC® CRL-1573™). The AD5 stock solution was treated with Benzonase (50 units/ml), clarified by centrifugation (300 g for 20 min at 4° C.) and filtered across 0.45 µm sterile filters (Minisart®, Sartorius Stedim Biotech GmbH), resulting in a concentration of $4.5 \times 10^{9}$ particles/mL being obtained. This solution is called "AD5 solution".

The purification was carried out on a filtration unit, Vivapure® (SSB, Göttingen), containing the crosslinked cellulose hydrate membrane and having a pore size of from 3 to 5 µm and a membrane volume of 0.023 mL, connected to an Äkta system. Over the experiment, the absolute flow rate was constantly 0.3 mL/min. The membrane was first equilibrated with a mixture composed of buffer A (0.5 M NaCl, 0.05 M Tris, pH=7.0, conductivity 53.2 mS/cm) and buffer B (13.3% by weight of PEG 6000, 0.5 M NaCl, 0.05 M Tris, pH=7.0, conductivity 28.4 mS/cm) in the ratio of 1:4. The final concentration of PEG 6000 in the mixture was 10% by weight. For the binding of the AD5 particles, buffer A was replaced with the AD5 solution. The mixing operation was done in-line in a static mixer of the Äkta system. After altogether 55 mL of solution (13.7 mL of AD5 solution and 41.3 mL of buffer B) had been loaded, the membrane was washed. To this end, a mixture composed of buffer A and buffer B in the ratio of 1:4 was used again. The AD5 particles were eluted from the membrane by using 100% buffer A.

The AD5 particles were quantified by means of quantitative real-time PCR on an instrument from Roche Life Science (LC480) using the master mix Brilliant III Ultra-Fast SYBR® Green QPCR. The reference used was an AD5 internal standard of viral DNA.

The recovery rate of the purified AD5 virus from the elution was 82.3% with a binding capacity of $1.4 \times 10^{12}$ particles per ml of membrane volume.

Exemplary Embodiment 7: Influence of the Pore Size of a Crosslinked Cellulose Hydrate Membrane on the Performance Parameter Permeability Crosslinked cellulose hydrate membranes of the Hydrosart® membrane type (Sartorius Stedim Biotech GmbH)

having different pore sizes were compared with respect to their permeabilities in the application of PEG-containing solutions, as exist in the method according to the invention. To this end, membranes having two different pore sizes were subjected to flow-through by the PEG-containing solution under application of 1 bar of pressure; the flow-through was collected and determined volumetrically. The solution used corresponded to the mixture M composed of buffer A and B according to Exemplary Embodiment 1 and containing 12% PEG.

For comparison, the permeability of the membrane having the pore size of from 3 to 5 μm was set at 100%. In the case of the membrane having a pore size of 1 μm, the permeability was only 30.8% compared to the permeability of the membrane having a pore size of from 3 to 5 μm.

TABLE 5

Overview of parameters and measurement values in the determination of the influence of pore size on the performance parameter permeability for crosslinked cellulose hydrate membranes in the case of flow-through with the PEG-containing mixture M from Exemplary Embodiment 1

|  | Membrane 1 | Membrane 2 |
| --- | --- | --- |
| Pore size in μm | 3 to 5 | 1 |
| Mixture M containing 12% PEG Permeability (ml/min*bar*cm$^2$) | 86.6 | 35.7 |
| Comparison % | 100 | 30.8 |

Exemplary Embodiment 8: Influence of Sanitization on the Performance Parameter Permeability in the Comparison of Crosslinked and Uncrosslinked Cellulose Hydrate Membrane A crosslinked cellulose hydrate membrane of the Hydrosart® membrane type (Sartorius Stedim Biotech GmbH) of 1 μm pore size was compared with respect to its permeability in the application of PEG-containing solutions after sanitization, with an uncrosslinked cellulose hydrate membrane of 1 μm pore size.

To this end, the membranes were sanitized by application of 1 N sodium hydroxide solution for 30 min and equilibrated with buffer A (approx. 150 MV). Thereafter, permeabilities of the PEG-containing mixture M were determined, as described in Exemplary Embodiment 7.

TABLE 6

Overview of parameters and measurement values in the determination of the performance parameter permeability for crosslinked and uncrosslinked cellulose hydrate membranes after sanitization with sodium hydroxide solution

|  | Membrane 2 Crosslinked | Membrane 3 Uncrosslinked |
| --- | --- | --- |
| Mixture M containing 12% PEG Permeability (ml/min*bar*cm$^2$) | 35.5 | 5.56 |
| Comparison % | 100 | 14.1 |

After sanitization, the permeability of the uncrosslinked cellulose hydrate membrane for the PEG-containing mixture M according to Exemplary Embodiment 1 is only 14% in comparison with the crosslinked cellulose hydrate membrane.

The invention claimed is:

1. A method for purifying viruses or virus-like particles from a solution, comprising the following steps:

a) providing a mixture M composed of a first solution and a second solution, the first solution containing the viruses or the virus-like particles to be purified and impurities, and the second solution containing a polyalkylene glycol having two or three carbon atoms in the repeating unit, b) loading a crosslinked cellulose hydrate membrane with the mixture M from step a), with the viruses or the virus-like particles attaching to the outer and inner membrane surfaces and being retained, and c) eluting the viruses or virus-like particles retained in the crosslinked cellulose hydrate membrane using a solution which contains no polyalkylene glycol having two or three carbon atoms in the repeating unit or which contains at least 50% less polyalkylene glycol having two or three carbon atoms in the repeating unit than the mixture M from step a), with the result that the viruses or the virus-like particles are obtained in purified form in the eluate.

2. The method as claimed in claim 1, wherein an unpurified, clarified bioprocess solution is used as the first solution.

3. The method as claimed in claim 1, further comprising a step d) which is carried out between step b) and step c), in which step d) the loaded crosslinked cellulose hydrate membrane is washed with a solution which contains as much polyalkylene glycol having two or three carbon atoms in the repeating unit as the mixture M from step a).

4. The method as claimed in claim 1, further comprising a step e), in which step e) the crosslinked cellulose hydrate membrane is sanitized before the loading according to step b) by means of alkaline solution.

5. The method as claimed in claim 1, further comprising a step f), in which step f) the crosslinked cellulose hydrate membrane is equilibrated before the loading according to step b), in which it is flushed with a buffer-containing solution, which contains polyalkylene glycol having two or three carbon atoms in the repeating unit, until a constant conductivity and/or a constant UV signal is measured in the permeate.

6. The method as claimed in claim 1, wherein the first and second solutions, which contain the viruses or virus-like particles to be purified and impurities as well as polyalkylene glycol having two or three carbon atoms in the repeating unit, are mixed with the aid of a mixer.

7. The method as claimed in claim 1, wherein the contact time of the viruses or the virus-like particles with the second solution, which contains polyalkylene glycol having two or three carbon atoms in the repeating unit, is less than one minute before the loading step.

8. The method as claimed in claim 1, wherein the concentration of polyalkylene glycol having two or three carbon atoms in the repeating unit in the mixture M which is contacted with the crosslinked cellulose hydrate membrane is from 1 to 20% by weight, based on the total mass of the mixture M.

9. The method as claimed in claim 1, wherein the polyalkylene glycol having two or three carbon atoms in the repeating unit is selected from the group consisting of polyethylene glycol and polypropylene glycol or mixtures thereof.

10. The method as claimed in claim 1, wherein polyethylene glycol (PEG) having an average molar mass of from 600 to 10 000 daltons is selected.

11. The method as claimed in claim 1, wherein the recovery rate for purified viruses or virus-like particles in the eluate is more than 50%.

12. The method as claimed in claim 1, wherein the concentration of the viruses or the virus-like particles in the eluate is elevated by a factor of from 5 to 10 in comparison with the starting solution.

13. The method as claimed in claim 4, further comprising a step f), in which step f) the crosslinked cellulose hydrate membrane is equilibrated after the sanitization according to step e), in which it is flushed with a buffer-containing solution B, which contains polyalkylene glycol having two or three carbon atoms in the repeating unit, until a constant conductivity and/or a constant UV signal is measured in the permeate.

* * * * *